(12) United States Patent
Sagner et al.

(10) Patent No.: US 7,378,241 B2
(45) Date of Patent: *May 27, 2008

(54) METHOD FOR DETERMINING THE EFFICIENCY OF NUCLEIC ACID AMPLIFICATIONS

(75) Inventors: Gregor Sagner, Penzberg (DE); Karim Tabiti, Poecking (DE); Martin Gutekunst, Eberfing (DE); Richie Soong, Tutzing (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 433 days.

This patent is subject to a terminal disclaimer.

(21) Appl. No.: 10/810,101

(22) Filed: Mar. 25, 2004

(65) Prior Publication Data

US 2005/0009048 A1    Jan. 13, 2005

Related U.S. Application Data

(63) Continuation of application No. 09/823,712, filed on Mar. 30, 2001.

(30) Foreign Application Priority Data

| Mar. 31, 2000 | (EP) | .................................. 00107036 |
| Jul. 13, 2000 | (DE) | ............................... 100 34 209 |
| Sep. 13, 2000 | (DE) | ............................... 100 45 521 |

(51) Int. Cl.
*C12Q 1/68*     (2006.01)
*C12P 19/34*    (2006.01)
*C07H 21/04*    (2006.01)

(52) U.S. Cl. ........................ 435/6; 435/91.2; 536/24.33
(58) Field of Classification Search .................... 435/6, 435/91.2; 536/24.31, 24.32, 24.33
See application file for complete search history.

(56) References Cited

U.S. PATENT DOCUMENTS

| 2,516,655 | A | 7/1950 | Smith |
| 3,163,404 | A | 12/1964 | Kraft et al. |
| 3,614,434 | A | 10/1971 | Horwitz |
| 3,711,379 | A | 1/1973 | Adams |
| 5,499,872 | A | 3/1996 | Baxter |
| 5,580,524 | A | 12/1996 | Forrest et al. |
| 5,858,658 | A | 1/1999 | Haemmerie et al. |
| 6,143,496 | A | 11/2000 | Brown et al. |
| 6,174,670 | B1 * | 1/2001 | Wittwer et al. ................. 435/6 |
| 6,232,079 | B1 | 5/2001 | Wittwer et al. |
| 6,235,504 | B1 | 5/2001 | Zhang et al. |
| 6,691,041 | B2 * | 2/2004 | Sagner et al. .................. 702/19 |
| 7,125,691 | B2 * | 10/2006 | Sagner et al. ............... 435/91.2 |
| 2002/0058262 | A1 | 5/2002 | Sagner et al. |

FOREIGN PATENT DOCUMENTS

| EP | 0 640 828 A1 | 8/1994 |
| EP | 0 959 140 A2 | 6/1999 |
| EP | 1138784 A2 | 2/2001 |
| EP | 01 10 7737 | 2/2003 |
| EP | 01 10 7738 | 3/2003 |
| WO | WO 97/46707 A1 | 12/1997 |
| WO | WO 99/54510 | 10/1999 |
| WO | WO 9954510 A2 * | 10/1999 |

OTHER PUBLICATIONS

Bourinbaiar et al., "Simple Procedure For Estimating The Efficiency of PCR," Molecular Biotechnology (1996) 6:87-90.
Fujii et al., "Mutation Detection by TaqMan-Allele Specific Amplification: Application to Molecular Diagnosis of Glycogen Storage Disease Type Ia and Medium Chain Acyl-CoA Dehydrogenase Deficiency," Human Mutation (2000) 15:189-196.
Isono K. "A Novel Quantitative PCR With Fluorogenic Probe," The Japanese Journal of Clinical Pathology, (1997) 45 218-223 Abstract.
LightCycler System. Roche Molecular Biochemicals (1999) 1-6.
Rodriguez-Antona et al., "Quantitative RT-PCR Measurement of Human Cytochrome P-450s: Application to Drug Induction Studies," (2000) Archives of Biochemistry and Biophysics 376:109-116.
Gibson, Ursula E. M. et al.; "A Novel Method for Real Time Quantitative RT-PCR"; 1995, *Genome Research*, vol. 6, pp. 995-1001.
Meijerink et al. A novel method to compensate for different amplification efficiencies between patient DNA samples in quantitative real-time PCR. *J Mol Diagnostics*, vol. 3, No. 2, pp. 55-61, 2001.

* cited by examiner

*Primary Examiner*—Suryaprabha Chunduru
(74) *Attorney, Agent, or Firm*—Charles M. Doyle; Townsend and Townsend and Crew, LLP

(57) ABSTRACT

The present invention concerns a method for determining the efficiency of the amplification of a target nucleic acid comprising the following steps: (i) preparation of a dilution series of the target nucleic acid, (ii) amplifying the target nucleic acid under defined reaction conditions, the amplification being measured in real-time (iii) setting a defined signal threshold value, (iv) determining the cycle number at which the signal threshold value is exceeded for various dilutions, (v) determining the amplification efficiency as a function of the amount of original target nucleic acid. The present invention also concerns a method for the quantification of a target nucleic acid in a sample in which the efficiency of the amplification reaction is determined in this manner and is taken into account in the quantification.

6 Claims, 3 Drawing Sheets

SEQUENCE LISTING

<160> NUMBER OF SEQ ID NOS: 8

<210> SEQ ID NO 1
<211> LENGTH: 18
<212> TYPE: DNA
<213> ORGANISM: Homo sapiens

<400> SEQUENCE: 1
ggccgcgtct cctttgag                                                 18

<210> SEQ ID NO 2
<211> LENGTH: 23
<212> TYPE: DNA
<213> ORGANISM: Homo sapiens

<400> SEQUENCE: 2
cgagttgtcc acagtcagca atg                                           23

<210> SEQ ID NO 3
<211> LENGTH: 20
<212> TYPE: DNA
<213> ORGANISM: Homo sapiens

<400> SEQUENCE: 3

-continued

```
ggccatggag cgctttgggt                                               20

<210> SEQ ID NO 4
<211> LENGTH: 26
<212> TYPE: DNA
<213> ORGANISM: Homo sapiens

<400> SEQUENCE: 4
aatggcaaga ccagcaagaa gatcac                                        26

<210> SEQ ID NO 5
<211> LENGTH: 19
<212> TYPE: DNA
<213> ORGANISM: Homo sapiens

<400> SEQUENCE: 5
cacacagcct actttccaa                                                19

<210> SEQ ID NO 6
<211> LENGTH: 17
<212> TYPE: DNA
<213> ORGANISM: Homo sapiens

<400> SEQUENCE: 6
ggtacccacg cgaatca                                                  17

<210> SEQ ID NO 7
<211> LENGTH: 22
<212> TYPE: DNA
<213> ORGANISM: Homo sapiens

<400> SEQUENCE: 7
taacggcaat gcggctgcaa cg                                            22

<210> SEQ ID NO 8
<211> LENGTH: 24
<212> TYPE: DNA
<213> ORGANISM: Homo sapiens

<400> SEQUENCE: 8
cggaagaaaa cagcccaaag atga                                          24
```

METHOD FOR DETERMINING THE EFFICIENCY OF NUCLEIC ACID AMPLIFICATIONS

The present application claims priority to co-pending European Patent Application No. 00107036.6, filed Mar. 31, 2000, co-pending German Patent Application No. 10034209.4, filed Jul. 13, 2000, and co-pending German Patent Application No. 10045521.2, filed Sep. 13, 2000, each of which is incorporated by reference herein in its entirety.

FIELD OF THE INVENTION

The present invention relates to the field of nucleic acid quantification with the aid of quantitative real-time PCR.

BACKGROUND OF THE INVENTION

Methods for the quantification of nucleic acids are important in many areas of molecular biology and in particular for molecular diagnostics. At the DNA level such methods are used for example to determine the copy numbers of gene sequences amplified in the genome. However, methods for the quantification of nucleic acids are used especially in connection with the determination of mRNA quantities since this is usually a measure for the expression of the respective coding gene.

If a sufficient amount of sample material is available, special mRNAs can be quantified by conventional methods such as Northern Blot analysis or RNAse protection assay methods. However, these methods are not sensitive enough for sample material that is only available in small amounts or for genes that express very weakly.

The so-called RT-PCR is a much more sensitive method. In this method a single-stranded cDNA is firstly produced from the mRNA to be analysed using a reverse transcriptase. Subsequently a double-stranded DNA amplification product is generated with the aid of PCR.

A distinction is made between two different variants of this method:

In the so-called relative quantification the ratio of the expression of a certain target RNA is determined relative to the amount of RNA of a so-called housekeeping gene which is assumed to be constitutively expressed in all cells independent of the respective physiological status. Hence the mRNA is present in approximately the same amount in all cells.

The advantage of this is that different initial qualities of the various sample materials and the process of RNA preparation has no influence on the particular result. However, an absolute quantification is not possible with this method.

Alternatively the absolute amount of RNA used can be determined with the aid of standard nucleic acids of a known copy number and amplification of a corresponding dilution series of this standard nucleic acid. There are two alternatives:

When using external standards the standard and target nucleic acid are amplified in separate reaction vessels. In this case a standard can be used with an identical sequence to the target nucleic acid. However, systematic errors can occur in this type of quantification if the RNA preparation to be analysed contains inhibitory components which impair the efficiency of the subsequent PCR reaction. Such errors can be excluded by using internal standards i.e. by amplifying the standard and target nucleic acid in one reaction vessel. However, a disadvantage of this method is that standards have to be used that have different sequences compared to the target nucleic acid to be analysed in order to be able to distinguish between the amplification of the standard and target nucleic acid. This can in turn lead to a systematic error in the quantification since different efficiencies of the PCR amplification cannot be excluded when the sequences are different.

PCR products can be quantified in two fundamentally different ways:

a) End point determination of the amount of PCR product formed in the plateau phase of the amplification reaction In this case the amount of PCR product formed does not correlate with the amount of the initial copy number since the amplification of nucleic acids at the end of the reaction is no longer exponential and instead a saturation is reached. Consequently different initial copy numbers exhibit identical amounts of PCR product formed. Therefore the competitive PCR or competitive RT-PCR method is usually used in this procedure. In these methods the specific target sequence is coamplified together with a dilution series of an internal standard of a known copy number. The initial copy number of the target sequence is extrapolated from the mixture containing an identical PCR product quantity of standard and target sequence (Zimmermann and Mannhalter, Bio-Techniques 21:280-279, 1996). A disadvantage of this method is also that measurement occurs in the saturation region of the amplification reaction.

b) Kinetic real-time quantification in the exponential phase of PCR.

In this case the formation of PCR products is monitored in each cycle of the PCR. The amplification is usually measured in thermocyclers which have additional devices for measuring fluorescence signals during the amplification reaction. A typical example of this is the Roche Diagnostics LightCycler (Cat. No. 20110468). The amplification products are for example detected by means of fluorescent labelled hybridization probes which only emit fluorescence signals when they are bound to the target nucleic acid or in certain cases also by means of fluorescent dyes that bind to double-stranded DNA. A defined signal threshold is determined for all reactions to be analysed and the number of cycles $C_p$ required to reach this threshold value is determined for the target nucleic acid as well as for the reference nucleic acids such as the standard or housekeeping gene. The absolute or relative copy numbers of the target molecule can be determined on the basis of the $C_p$ values obtained for the target nucleic acid and the reference nucleic acid (Gibson et al., Genome Research 6:995-1001; Bieche et al., Cancer Research 59:2759-2765, 1999; WO 97/46707; WO 97/46712; WO 97/46714). Such methods are also referred to as a real-time PCR.

In summary in all the described methods for the quantification of a nucleic acid by PCR the copy number formed during the amplification reaction is always related to the copy number formed of a reference nucleic acid which is either a standard or an RNA of a housekeeping gene. In this connection it is assumed that the PCR efficiency of the target and reference nucleic acid are not different.

Usually a PCR efficiency of 2.00 is assumed which corresponds to a doubling of the copy number per PCR cycle (User Bulletin No. 2 ABI Prism 7700, PE Applied Biosystems, 1997).

However, it has turned out that the real PCR efficiency can be different from 2.00 since it is influenced by various factors such as the binding of primers, length of the PCR product, G/C content and secondary structures of the nucleic acid to be amplified and inhibitors that may be present in the reaction mixture as a result of the sample preparation. This is particularly relevant when using heterologous reference nucleic acids e.g. in the relative quantification compared to the expression of housekeeping genes. Moreover it is also not known whether or to what extent the initial concentration of the target nucleic acid to be detected significantly influences the efficiency of an amplification reaction.

SUMMARY OF THE INVENTION

The object of the present invention was therefore to provide a method to determine the efficiency of nucleic acid amplifications as exactly as possible and its use in methods for the exactest possible quantification of nucleic acids.

This object is achieved according to the invention by a method for determining the efficiency of the amplification of a target nucleic acid wherein
  a) a dilution series of the target nucleic acid is prepared
  b) the target nucleic acid is amplified under defined reaction conditions and the amplification is measured in real-time
  c) a defined signal threshold value is set
  d) for each dilution the cycle number is determined at which the signal threshold value is exceeded,
  e) the amplification efficiency is determined as a function of the original amount of target nucleic acid.

Thus the amplification efficiency can be determined by generating a non-linear continuously differentiable function of a logarithm of the copy number of target nucleic acid used for the amplification as a function of the cycle number at which the signal threshold value is exceeded and from this function the amplification efficiency E is calculated as a function of the amount of target nucleic acid. In this embodiment the amplification efficiency E of a certain amount of target nucleic acid is preferably determined as the negative local first derivative of the continuously-differentiable function from step e).

Alternatively the amplification efficiency can also be determined by determining a non-linear continuously differentiable function of the determined cycle numbers as a function of the logarithm of the copy numbers of target nucleic acid used for the amplification and calculating the amplification efficiency E from the determined function. In this case the amplification efficiency E of a certain amount of target nucleic acid is preferably determined as the reciprocal negative local first derivative of the continuously differentiable function from step e).

Methods have proven to be particularly advantageous in which the amplification efficiency is determined as a function of the logarithm of the concentration of the target nucleic acid or vice versa with the aid of a polynomial fit to determine the non-linear continuously differentiable function. This can be a polynomial fit of the $3^{rd}$, $4^{th}$, $5^{th}$, $6^{th}$, or $7^{th}$ degree or preferably a fit of the $4^{th}$ degree.

Hence methods according to the invention for the quantification of a target nucleic acid in a sample comprise the following steps:

a) Determination according to the invention of the amplification efficiency of the target nucleic acid under defined conditions.
  b) Amplification of the target nucleic acid contained in the sample under the same reaction conditions.
  c) Measurement of the amplification in real-time.
  d) Quantification of the original amount of target nucleic acid in the sample by correction of the original amount derived from step c) with the aid of the determined amplification efficiency.

These methods can be used for relative quantification in comparison to the expression of housekeeping genes as well as for absolute quantification.

According to the invention methods for the absolute quantification of the target nucleic acid in a sample comprise the following steps:
  a) Determination according to the invention of the amplification efficiencies of the target nucleic acid and of an internal or external standard under defined amplification conditions.
  b) Amplification of the target nucleic acid contained in the sample and of the internal or external standard under the same defined reaction conditions.
  c) Measurement of the amplification of the target nucleic acid and standard in real-time.
  d) Calculation of the original copy number in the sample by correction of the copy number derived in step c) with the aid of the amplification efficiencies determined in step a).

In contrast methods for the quantification of a target nucleic acid in a sample relative to a reference nucleic acid comprise the following steps.
  a) Determination according to the invention of the amplification efficiencies of the target nucleic acid and of the reference nucleic acid under defined amplification conditions.
  b) Amplification of the target nucleic acid contained in the sample as well as of the reference nucleic acid contained in the sample under the same defined amplification conditions.
  c) Measurement of the amplification of the target nucleic acid and of the reference nucleic acid in real-time.
  d) Calculation of the original ratio of target nucleic acid and reference nucleic acid in the sample by correction of the ratio derived from step c) with the aid of the amplification efficiencies determined in step a).

The invention additionally concerns all methods in which the determination of the amplification efficiencies is only indirectly used for the quantification result and in particular one which is dependent on the initial concentration. In this sense the invention concerns in particular a method for the relative quantification of a target nucleic acid relative to a reference nucleic acid and standardized with reference to a calibrator sample comprising the following steps:
  a) Preparation of one common or two separate dilution series of target nucleic acid and reference nucleic acid.
  b) Amplification of the various dilutions of target nucleic acid and reference nucleic acid under defined reaction conditions, the amplification of the nucleic acid being measured in real-time.
  c) Setting defined signal threshold values for the target nucleic acid and reference nucleic acid.
  d) Determining the cycle numbers Cp at which the defined signal threshold values for the target nucleic acid and reference nucleic acid are exceeded in each dilution.
  e) Determination of a continuously differentiable function of the logarithm of the amount of target nucleic acid used as a function of the Cp values determined in d) and determination of a continuously differentiable function of the logarithm of the amounts of reference nucleic acid used as a function of the determined Cp values.
f) Determination of the Cp values of the target nucleic acid and reference nucleic acid in the sample to be analysed as well as in a calibrator sample.
g) Assignment of the Cp values measured in step f) to particular function values of the functions determined in step e).
h) Determining the quotients of the function values from g) of the target nucleic acid and reference nucleic acid for the sample to be analysed as well as for the calibrator sample.
i) Determination of the ratio of the quotients from h) as a measure for the original amount of target DNA contained in the sample.

DETAILED DESCRIPTION OF THE INVENTION

Figure 1:
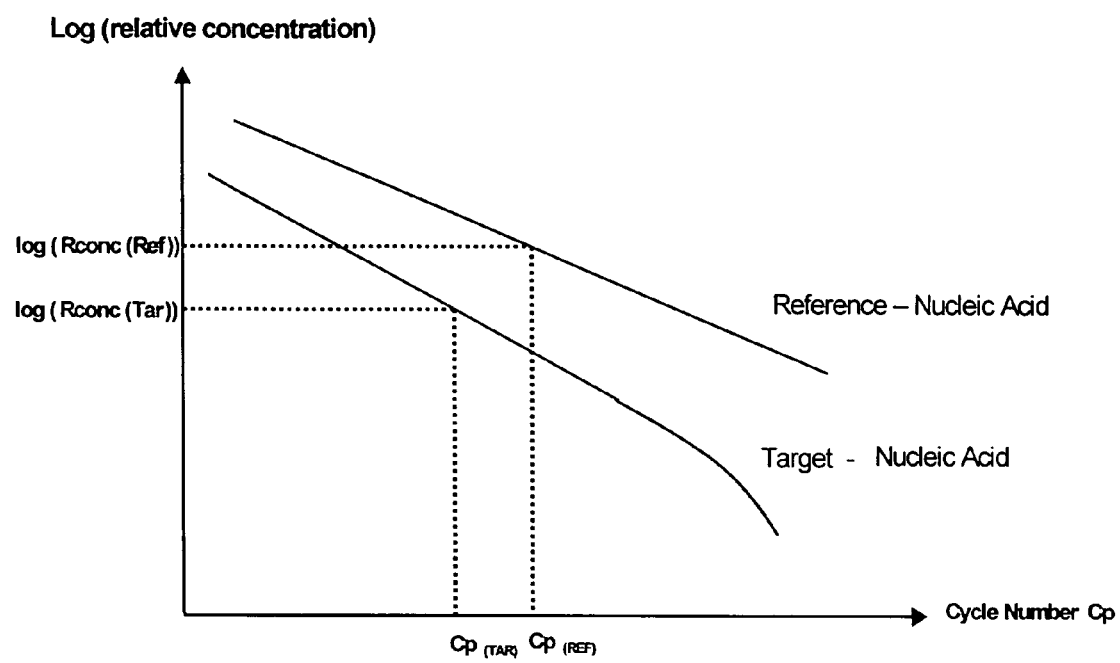
FIG. 1:
Schematic representation of a function for determining the logarithm of a relative concentration versus the determined cycle number.

A) Requirement for a Target-dependent Efficiency Correction

The importance of an efficiency correction for quantitative nucleic acid amplification methods will be illustrated by an error calculation. Table 1 shows a theoretical calculation of the average percentage error of the determined copy number in the case of amplification efficiencies that are different from 2.00 in relation to the respective cycle number. The error is calculated according to the formula percentage error=$(2^n/E^n-1)\times 100$ in which E is the efficiency of the amplification and n is the respective cycle number at which the percentage error is determined.

TABLE 1

| PCR efficiency | Detection Cycle (n) | | | | | |
|---|---|---|---|---|---|---|
| (E) | 10 | 15 | 20 | 25 | 30 | 35 |
| 2.00 | — | — | — | — | — | — |
| 1.97 | 16% | 25% | 35% | 46% | 57% | 70% |
| 1.95 | 29% | 46% | 66% | 88% | 113% | 142% |
| 1.90 | 67% | 116% | 179% | 260% | 365% | 500% |
| 1.80 | 187% | 385% | 722% | 1290% | 2260% | 3900% |
| 1.70 | 408% | 1045% | 2480% | 5710% | 13.000% | 29.500% |
| 1.60 | 920% | 2740% | 8570% | 26.400% | 80.700% | 246.400% |

The amplification efficiency of a PCR reaction can be determined by various methods.

For example in the case of a real-time monitoring of PCR reactions this can be achieved by determining the amount of amplified target nucleic acid in each amplification cycle and determining the efficiency of the amplification reaction from the resulting values.

Alternatively the efficiency of the amplification reaction of a particular target can be determined in a real-time PCR mode under defined conditions by firstly amplifying various dilutions of the target nucleic acid and determining the cycle number for each dilution at which a previously defined signal threshold value is exceeded.

The efficiency is then determined from the slope of the function of the logarithm of the copy number used versus the cycle number determined for the respective copy number. An advantage of this method is that a systematic error cannot occur that results from determining the amplification efficiency in a phase of the PCR reaction in which there is no longer an exponential amplification of the target nucleic acid (plateau phase).

However, it unexpectedly turned out that under certain circumstances the amplification efficiency can also be dependent on the original amount of target nucleic acid. An obvious change in the amplification efficiency is found especially at low concentrations in the corresponding experimental preparations. Consequently the methods described above for determining the efficiency do not result in linear functions so that in these cases the described determination of the slope of the regression line would for example result in values for the determined amplification efficiencies that are too low especially at low concentrations of target nucleic acid.

Due to the dependence of the amplification efficiency on the concentration of the target nucleic acid, it is not possible to rule out a change in the amplification efficiency even already during the first cycles of an amplification reaction although it is still in an exponential phase. Since, however, this phenomenon cannot be directly experimentally analysed due to a lack of detection sensitivity, a concentration-dependent amplification efficiency is understood in the following as the amplification efficiency determined by means of the elapsed cycles at the respective detection time point.

B) Absolute and Relative Quantification

The present invention therefore concerns methods for the efficiency-corrected quantification of nucleic acids in which the efficiency of the amplification is determined by a) preparing a dilution series of the target nucleic acid
b) amplifying the target nucleic acid under defined reaction conditions as claimed in claim 1 and measuring the amplification of the nucleic acid in real-time
c) setting a defined signal threshold value
d) for each dilution determining the cycle number Cp at which the signal threshold value is exceeded and
e) determining the amplification efficiency as a function of the amount of target nucleic acid.

In particular the amplification efficiency can be determined as a function of the original amount of target nucleic acid by
 a non-linear continuously differentiable function of a logarithm of the copy number of target nucleic acid used for the amplification as a function of the copy number at which the signal threshold value is exceeded or alternatively a non-linear continuously differentiable function of the determined cycle number as a function of the logarithm of the copy number of target nucleic acid used in each case and calculating the amplification efficiency E from the determined function. The respective amplification efficiency is determined according to the invention as a function of the amount of target nucleic acid that is used in each case.

The continuous function is determined by suitable mathematical methods and algorithms. For example the function can be described by a polynomial fit of higher degree. A polynomial fit of the $3^{rd}$, $4^{th}$, $5^{th}$, $6^{th}$ or $7^{th}$ degree has proven to be suitable for calculating a function, a polynomial fit of the $4^{th}$ order being preferred.

The efficiency which depends on the target amounts can be determined by derivation of a continuously differentiable function F(Cp) of the Cp values as a function of a logarithm of the original copy number or vice versa.

The amplification efficiency can then be determined according to the equation $$E = G^{-f(Cp)}$$

in which f(Cp) is the derivative of the continuous function and G is the base number of the logarithm. Hence in this embodiment the amplification efficiency E of a certain original amount of target nucleic acid is determined as the negative local first derivative of the previously determined continuously differentiable function.

Alternatively the amplification efficiency E can be determined according to the equation $$E = G^{-\frac{1}{f'(\log(conc))}}$$

in which conc is the original amount of the nucleic acid, f(log(conc)) is the derivative of the continuous function and G is the base number of the logarithm. Hence in this embodiment the amplification efficiency E of a certain original amount of target nucleic acid is determined as the reciprocal negative local first derivative of the previously determined continuously differentiable function.

The efficiency-corrected quantification of nucleic acids as a function of the amount of target nucleic acid can in principle be used for methods for absolute quantification as well as for methods for relative quantification. Moreover such an efficiency correction is also particularly advantageous in methods in which a relative quantification is standardized on the basis of a so-called calibrator sample (ABI Prism 7700 Application Manual, Perkin Elmer) in order to eliminate the influence of different detection sensitivities for the target and reference nucleic acid.

If it is intended to determine the absolute amount of target nucleic acid to be detected in the sample, the method for quantifying a target nucleic acid in a sample according to the invention comprises the following steps:
  a) Determination of the amplification efficiencies of the target nucleic acid and of an internal or external standard as a function of their respective initial concentrations under defined amplification conditions.
  b) Amplification of the target nucleic acid contained in the sample and of the internal or external standard under the same defined reaction conditions.
  c) Measurement of the amplification of the target nucleic acid and standard in real-time.
  d) Calculation of the original copy number in the sample by correction of the copy number derived in step c) with the aid of the amplification efficiencies determined in step a).

The sequences of the target nucleic acid and standard nucleic acid are advantageously substantially identical. However, when selecting the sequence for an internal standard it must be taken into account that the available detection system is able to distinguish between the standard and target nucleic acid. This can for example be achieved by using hybridization probes with different labels for the detection of the target nucleic acid and internal standard. Ideally oligonucleotides are used for this as detection probes which can be used to distinguish between minimal sequence differences such as point mutations.

An advantage of using an internal standard is that the inhibitors present in the sample also influence the amplification of the standard. Hence differences in the amplification efficiencies can be minimized.

In contrast the use of an external standard has the advantage that the amplification reactions of the target nucleic acid and standard cannot competitively interfere with one another with regard to their efficiency. Moreover the amplification products of the standard and target nucleic acid can be detected in parallel reaction mixes with the aid of the same detection system for example with the same hybridization probe. A disadvantage is possible differences in the PCR efficiencies due to inhibitors in the sample. However, errors in the quantification caused by this can be eliminated by an efficiency correction according to the invention.

A subject matter of the present invention in relation to relative quantification is also a method for the quantification of a target nucleic acid in a sample relative to a reference nucleic acid comprising the following steps:
  a) Determination of the amplification efficiencies of the target nucleic acid and of the reference nucleic acid as a function of their respective initial concentrations under defined amplification conditions.
  b) Amplification of the target nucleic acid contained in the sample as well as of the reference nucleic acid contained in the sample under the same defined amplification conditions.
  c) Measurement of the amplification of the target nucleic acid and of the reference nucleic acid in real-time.
  d) Calculation of the original ratio of target nucleic acid and reference nucleic acid in the sample by correction of the ratio derived from step c) with the aid of the amplification efficiencies determined in step a).

Such a method according to the invention eliminates on the one hand the influence of inhibitors that may be present in the examined sample and, on the other hand, corrects errors which may occur as a result of different amplification efficiencies of the target nucleic acid and reference nucleic acid.

An essential requirement for this method according to the invention for relative quantification is that the amplification efficiency of the target nucleic acid as well as the amplification efficiency of the reference nucleic acid is determined as a function of the amount of target and reference nucleic acid that was originally present. Both of these determinations are preferably carried out by the method described above by determining the cycle number at which a certain signal threshold value is exceeded.

In a preferred embodiment of relative quantification the sample is divided into two aliquots and the real-time measurement of the amplification of the target nucleic acid and reference nucleic acid is carried out in separate reaction vessels. This prevents interference between the amplification reactions of the target nucleic acid and the reference nucleic acid with regard to their efficiency for example by competition for deoxynucleotides or Taq polymerase. Furthermore the target nucleic acid and reference nucleic acid can be detected with the same detection systems for example with the same DNA binding dye.

Alternatively the real-time measurement of the amplification of target nucleic acid and reference nucleic acid can be carried out from one sample in the same reaction vessel using differently labelled hybridization probes. This is particularly advantageous when only small amounts of sample material are available because the number of PCR reactions required is halved in this manner.

Steps b) to d) are advantageously carried out in a parallel mixture containing a so-called calibrator sample. The calibrator sample is a sample which contains the target nucleic acid and reference nucleic acid in a defined ratio that is constant for each measurement. Subsequently the ratio of the quotients determined for the sample and for the calibrator sample is determined as a measure for the original amount of target nucleic acid in the sample. This has the advantage that in addition other systematic errors are eliminated that are due to differences in the detection sensitivity of the target nucleic acid and reference nucleic acid. Such systematic errors can for example occur as a result of different hybridization properties of the hybridization probes or , in the case of fluorescent-labelled probes, different excitation efficiencies, quantum yields or coupling efficiencies of the dye to the probe. Therefore the sample to be tested and the calibrator sample must be analysed in each experiment with the same detection agents i.e. with the same batch of fluorescent-labelled hybridization probes.

The invention in particular also concerns those embodiments of the described methods for the efficiency-corrected quantification of nucleic acids in which the amplification products are detected by hybridization probes which can be labelled with a detectable component in many different ways.

A prerequisite for the efficiency-corrected determination of the original amount of a target nucleic acid and for the determination of the amplification efficiencies per se is to set signal threshold values and subsequently determine the cycle number for the respective amplification reaction at which a certain signal threshold value is reached. The signal threshold value can be determined according to the prior art in various ways:

According to the prior art the signal threshold value can for example be a signal which corresponds to a certain multiple of the statistical variance of the background signal (ABI Prism 7700 Application Manual, Perkin Elmer).

Alternatively the cycle number at which the signal threshold value is exceeded can be determined according to the so-called "fit point above threshold" method (LightCycler Operator's Manual, B59-B68, Roche Molecular Biochemicals, 1999).

In a further embodiment the threshold value can be determined as a relative value instead of an absolute value when, independently of the absolute value of the signal, the course of the amplification reaction is determined as a function of the cycle number and subsequently the $n^{th}$ derivative is calculated. In this case exceeding certain extremes can be defined as exceeding a certain signal threshold value (EP Application No. 00106523.4). Hence this method of determining the threshold value is independent of the absolute signal strength of for example a fluorescence signal. Thus it is particularly suitable for those embodiments in which the target nucleic acid and reference nucleic acid are amplified in the same reaction vessel and are detected with the aid of different fluorescent labels. Methods have proven to be particularly suitable for the efficiency-corrected quantification of PCR products in which the maximum of the second derivative is determined as a measure for the signal threshold value.

The hybridization probes used for the method according to the invention are usually single-stranded nucleic acids such as single-stranded DNA or RNA or derivatives thereof or alternatively PNAs which hybridize at the annealing temperature of the amplification reaction to the target nucleic acid. These oligonucleotides usually have a length of 20 to 100 nucleotides.

The labelling can be introduced on any ribose or phosphate group of the oligonucleotide depending on the particular detection format. Labels at the 5' and 3' end of the nucleic acid molecule are preferred.

The type of label must be detected in the real-time mode of the amplification reaction. This is for example in principle also (but not only) possible with the aid of labels that can be detected by NMR.

Methods are particularly preferred in which the amplified nucleic acids are detected with the aid of at least one fluoresent-labelled hybridization probe.

Many test procedures are possible. The following three detection formats have proven to be particularly suitable in connection with the present invention:

(i) FRET Hybridization Probes

For this test format 2 single-stranded hybridization probes are used simultaneously which are complementary to adjacent sites of the same strand of the amplified target nucleic acid. Both probes are labelled with different fluorescent components. When excited with light of a suitable wavelength, a first component transfers the absorbed energy to the second component according to the principle of fluorescence resonance energy transfer such that a fluorescence emission of the second component can be measured when both hybridization probes bind to adjacent positions of the target molecule to be detected.

Alternatively it is possible to use a fluorescent-labelled primer and only one labelled oligonucleotide probe (Bernard et al., Analytical Biochemistry 235, p. 1001-107 (1998)).

(ii) TAQMAN® Hybridization Probes

A single-stranded hybridization probe is labeled with two components. When the first component is excited with light of a suitable wavelength, the absorbed energy is transferred to the second component, the so-called quencher, according to the principle of fluorescence resonance energy transfer. During the annealing step of the PCR reaction, the hybridization probe binds to the target DNA and is degraded by the 5'-3' exonuclease activity of the Taq polymerase during the subsequent elongation phase. As a result the excited fluorescent component and the quencher are spatially separated from one another and thus a fluorescence emission of the first component can be measured.

(iii) Molecular Beacons

These hybridization probes are also labelled with a first component and with a quencher, the labels preferably being located at both ends of the probe. As a result of the secondary structure of the probe, both components are in spatial vicinity in solution. After hybridization to the target nucleic acids both components are separated from one another such that after excitation with light of a suitable wavelength the fluorescence emission of the first component can be measured (Lizardi et al., U.S. Pat. No. 5,118,801).

In the described embodiments in which only the target nucleic acid or only the reference nucleic acid or an external standard is amplified in one reaction vessel in each case, the respective amplification product can also be detected according to the invention by a DNA binding dye which emits a corresponding fluorescence signal upon interaction with the double-stranded nucleic acid after excitation with light of a suitable wavelength. The dyes SybrGreen and SybrGold (Molecular Probes) have proven to be particularly suitable for this application. Intercalating dyes can alternatively be used.

C) Efficiency Correction by the Direct Determination of the Amplification Efficiencies Absolute Quantification In a preferred embodiment for the absolute quantification of a target nucleic acid in a sample the method according to the invention comprises the following steps:
  a) Determination of the amplification efficiencies of the target nucleic acid and of an internal or external standard as a function of the respective initial amounts under defined amplification conditions
  b) Amplification of the target nucleic acid contained in the sample and of the internal or external standard under the same defined reaction conditions.
  c) Measurement of the amplification of the target nucleic acid and standard in real-time.
  d) Determination of a defined signal threshold value.
  e) Determination of the cycle numbers at which the signal threshold value is in each case exceeded during the amplification of the target nucleic acid and the standard.
  f) Determination of the original copy number $N(T)_0$ of the target nucleic acid in the sample according to the formula $$N(T)_0 = N(S)_0 * \frac{E(S)^{ns}}{E(T)^{nt}}$$

$N(S)_0$=the original amount of standard used
$E(S)$=the amplification efficiency of the standard for a particular cycle n at the respective time point of the detection averaged over the elapsed cycles
$E(T)$=the amplification efficiency of the target for a particular cycle n at the respective time point of the detection averaged over the elapsed cycles
ns=the cycle number at which the signal threshold value is exceeded by the amplification of the standard nucleic acid and
nt=the cycle number at which the signal threshold value is exceeded by the amplification of the target nucleic acid Under these circumstances the calculation of $N(T)_0$ results in:

$N(T)_n = N(T)_0 * E^{nt}$ and $N(S)_n = N(S)_0 * E^{ns}$

Since an identical signal threshold value has been set for the target and standard nucleic acid this approximates to:

$N(T)_n = N(S)_n$,

Hence the original copy number of target nucleic acid present in the sample is calculated according to the equation $$N(T)_0 = N(S)_0 * \frac{E(S)^{ns}}{E(T)^{nt}}$$

In an alternative embodiment for the absolute quantification of a target nucleic acid in a sample the method according to the invention comprises the following steps:
  a) Determination of the amplification efficiencies of the target nucleic acid and of an internal or external standard as a function of the respective initial amounts under defined amplification conditions
  b) Amplification of the target nucleic acid contained in the sample and of the internal or external standard under the same defined reaction conditions.
  c) Measurement of the amplification of the target nucleic acid and standard in real-time.
  d) Determination of a defined signal threshold value.
  e) Determination of the cycle numbers at which the signal threshold value is in each case exceeded during the amplification of the target nucleic acid and the standard.
  f) Determination of the original copy number $N(T)_0$ of the target nucleic acid in the sample according to the formula $$N(T)_0 = N(S)_0 * \frac{\prod_{1-n} E(S_x)}{\prod_{1-n} E(T_x)}$$

$N(S)_0$=the original amount of standard used
$E(S_n)$=the amplification efficiency of the standard for an individual cycle x
$E(T_n)$=the amplification efficiency of the target for an individual cycle x $\prod_{1-n} E(S_x)$ = the product of the efficiencies determined for all cycles of the amplification of the standard until the signal threshold value is reached at cycle $n$ $\prod_{1-n} E(T_x)$ = the product of the efficiencies determined for all cycles of the amplification of the target nucleic acid until the signal threshold value is reached at cycle $n$ In this case the amplification efficiencies of the target nucleic acid and of the internal standard are preferably determined as described above by determining a cycle number at which a certain signal threshold value is exceeded.

N(T)₀ is calculated according to the invention as follows:

$$N(T)_n = N(T)_0 * E(T_1) * \ldots * E(T_n) = N(T)_0 * \prod_{1-n} E(T_x)$$

and $$N(S)_n = N(S)_0 * E(S_1) * \ldots * E(S_n) = N(S)_0 * \prod_{1-n} E(S_x)$$

Since an identical signal threshold value has been set for the target and standard nucleic acid this approximates to:

$$N(T)_n = N(S)_n,$$

Hence the original copy number of target nucleic acid present in the sample is calculated according to the equation $$N(T)_0 = N(S)_0 * \frac{\prod_{1-n} E(S_x)}{\prod_{1-n} E(T_x)}$$

A disadvantage of this method is that the efficiencies of the first cycles of each amplification reaction cannot be determined since the amount of amplified nucleic acid is still below the detection limit of any detection system available in the prior art.

However, the efficiency of an earlier cycle can be approximated as the geometric mean π of all the efficiencies determined for the following cycles. Alternatively the non-determinable efficiency of an early cycle can be equated with the efficiency determined for the first cycle in which an amplification product was detectable.

Relative Quantification

A special embodiment of the relative quantification according to the invention is a method for the quantification of a target nucleic acid in a sample relative to a reference nucleic acid comprising the following steps:

a) Determination of the amplification efficiencies of the target nucleic acid and of the reference nucleic acid as a function of the respective initial amounts under defined amplification conditions
b) Amplification of the target nucleic acid contained in the sample and of the reference nucleic acid contained in the sample under the same defined amplification conditions.
c) Measurement of the amplification of the target nucleic acid and the reference nucleic acid in real-time.
d) Determination of a defined signal threshold value.
e) Determination of the cycle numbers at which the signal threshold value is in each case exceeded during the amplification of the target nucleic acid and the reference nucleic acid.
f) Calculation of the original ratio of target nucleic acid and reference nucleic acid in the sample according to the formula $$N(T)_0 / N(R)_0 = \frac{E(R)^{nr}}{E(T)^{nt}}$$

N(T)₀=the original amount of target nucleic acid
N(R)₀=the original amount of reference nucleic acid
E(R)=the amplification efficiency of the reference nucleic acid averaged over the elapsed cycles at the respective detection time at a certain cycle n
E(T)=the amplification efficiency of the target nucleic acid averaged over the elapsed cycles at the respective detection time at a certain cycle n
nr=the cycle number at which the signal threshold value is exceeded by the amplification of the reference nucleic acid
nt=the cycle number at which the signal threshold value is exceeded by the amplification of the target nucleic acid Under these circumstances the calculation of N(T)₀ results in:

$$N(T)_n = N(T)_0 * E(T)^{nt} \text{ and}$$

$$N(R)_n = N(R)_0 * E(R)^{nr}$$

Since an identical signal threshold value has been set for the target and standard nucleic acid this approximates to:

$$N(T)_n = N(R)_n,$$

Hence the original copy number of target nucleic acid present in the sample is calculated according to the equation $$N(T)_0 / N(R)_0 = \frac{E(R)^{nr}}{E(T)^{nt}}$$

In an alternative embodiment for the relative quantification of a target nucleic acid in a sample the method according to the invention comprises the following steps:

a) Determination of the amplification efficiencies of the target nucleic acid and of the reference nucleic acid as a function of the initial amounts under defined amplification conditions
b) Amplification of the target nucleic acid contained in the sample and of the reference nucleic acid contained in the sample under the same defined amplification conditions.
c) Measurement of the amplification of the target nucleic acid and of the reference nucleic acid in real-time.
d) Determination of a defined signal threshold value.
e) Determination of the cycle numbers at which the signal threshold value is in each case exceeded during the amplification of the target nucleic acid and the reference nucleic acid.
f) Determination of the original ratio of the target nucleic acid and reference nucleic acid in the sample according to the formula $$N(T)_0 / N(R)_0 = \frac{\prod_{1-n} E(R_x)}{\prod_{1-n} E(T_x)}$$

N(T)₀=the original amount of target nucleic acid present in the sample $N(R)_0$=the original amount of reference nucleic acid present in the sample $E(R_n)$=the amplification efficiency of the reference nucleic acid in an individual cycle x $E(T_n)$=the amplification efficiency of the target nucleic acid in an individual cycle x $\prod_{1-n} E(T)$ = the product of the efficiencies determined for all cycles of the amplification of the target nucleic acid until the signal threshold value is reached at cycle $n$ $\prod_{1-n} E(R)$ = the product of the efficiencies determined for all cycles of the amplification of the reference nucleic acid until the signal threshold value is reached at cycle $n$ The ratio in step (f) is determined according to the invention as follows:

$$N(T)_n = N(T)_0 * ET_1 * \ldots E(T_n) = N(T)_0 \prod_{\substack{n=1 \\ 1-n}} E(T_x) \quad (1)$$

$$N(R)_n = N(R)_0 * E(R_1) * \ldots E(R_n) = N(R)_0 * \prod_{1-n} E(R_x) \quad (2)$$

wherein $N(T)_n$=the amount of target-DNA at the signal threshold value and $N(R)_n$=the amount of reference-DNA at the signal threshold value from (1) and (2) it follows that:

$$\frac{N(T)_n}{N(R)_n} = \frac{N(T)_0 * \prod_{1-n} E(T_x)}{N(R)_0 * \prod_{1-n} E(R_x)} \quad (3)$$

It follows that:

$$\frac{N(T)_0}{N(R)_0} = \frac{N(T)_n * \prod_{1-n} E(R_x)}{N(R)_n * \prod_{1-n} E(T_x)} \quad (4)$$

Since an identical signal threshold value is set for the target nucleic acid and reference nucleic acid it can be assumed that approximately $$N(T)_n = N(R)_n$$

Under this condition and starting from equation (4) for the original ratio of target nucleic acid and reference nucleic acid, this results in the equation $$N(T)_0 / N(R)_0 = \prod_{1-n} E(R_x) \Big/ \prod_{1-n} E(T_x) \quad (5)$$

Similarly to the absolute quantification, the efficiency of an early cycle that cannot be determined can be assumed to be the geometric average $\pi$ of all the efficiencies determined for the following cycles. Alternatively the efficiency of an early cycle can be equated with the efficiency that was determined for the first cycle in which an amplification product was detectable.

Relative Quantification and Standardization by Reference to a Calibrator

The approximation $N(T)_n = N(R)_n$ however only applies when the target nucleic acid and reference nucleic acid are detected with different sensitivities.

Due to the detection of the amplification products in this embodiment it is then advantageous to additionally carry out steps b), c), e) and f) of the method described above with a calibrator sample in order to eliminate systematic errors and subsequently to determine the ratio of the quotient determined for the sample and for the calibrator sample as a measure for the original amount of target nucleic acid in the sample.

Therefore according to the invention a calibrator sample is measured in a parallel reaction mixture and the ratio of the quotients $N(T)_0/N(R)_0$ is determined for the sample and for the calibrator sample as a measure for the original amount of target nucleic acid in the sample.

This results in the following from equation (4) using the indices $$\frac{N(T)_{0A}}{N(R)_{0A}} \Big/ \frac{N(T)_{0K}}{N(R)_{0K}} = \frac{\dfrac{N(T)_{nA} * \prod_{1-n} E_A(R_x)}{N(R)_{nA} * \prod_{1-n} E_A(T_x)}}{\dfrac{N(T)_{nK} * \prod_{1-n} E_K(R_x)}{N(R)_{nK} * \prod_{1-n} E_K(T_x)}} \quad (6)$$

Due to the fact that an identical signal threshold value has been defined the sample to be analysed and for the calibrator sample and that identical agents are used to detect target and reference amplicons in the sample and in the calibrator sample, the ratio of the quotients determined for the sample and for the calibrator sample are as follows:

$$\frac{N(R)_{nA}}{N(T)_{nA}} \Big/ \frac{N(R)_{nK}}{N(T)_{nK}} = 1$$

Hence the ratio of the quotients of the sample to be analysed and the calibrator sample is:

$$\frac{N(T)_{0A}}{N(R)_{0A}} \Big/ \frac{N(T)_{0K}}{N(R)_{0K}} = \frac{\prod_{1-n} E_A(R_x) * \prod_{1-n} E_K(T_x)}{\prod_{1-n} E_A(T_x) * \prod_{1-n} E_K(R_x)} \quad (7)$$

Consequently a relative value can be obtained for the original copy number of target nucleic acid in the sample in which systematic errors due to different amplification efficiencies as well as due to different detection sensitivities have been eliminated. The only requirement for the accuracy of the determined value is the justified assumption that under absolutely identical buffer conditions the amplification and detection efficiencies are also identical in the various reaction vessels.

D) Implicit Efficiency Correction When Using a Calibrator Sample

Furthermore the concentration-dependent efficiency correction according to the invention is also suitable for quantification methods in which the amplification efficiency is not determined directly but rather is incorporated indirectly in the quantification result.

This may for example be the case in methods for relative quantification in which the result is standardized on the basis of a calibrator sample in order to eliminate the influence of different detection sensitivities for the target and reference nucleic acid.

Hence the present invention also encompasses methods for the relative quantification of a target nucleic acid relative to a reference nucleic acid and standardized on the basis of a calibrator sample comprising the following steps:

a) Preparing a common or two separate dilution series of target nucleic acid and reference nucleic acid.
b) Amplifying the various dilutions of target nucleic acid and reference nucleic acid under defined reaction conditions, the amplification of the nucleic acid being measured in real-time.
c) Setting defined signal threshold values for the target nucleic acid and reference nucleic acid.
d) Determining the cycle numbers Cp at which the signal threshold values defined for the target nucleic acid and reference nucleic acid are exceeded in each dilution.
e) Determining a continuously differentiable function of the Cp values determined in d) as a function of a logarithm of the amounts used of target nucleic acid and determining a continuously differentiable function of the Cp values determined as a function of a logarithm of the amounts used of reference nucleic acid.
f) Determination of the Cp values for the target nucleic acid and the reference nucleic acid in the sample to be analysed as well as in a calibrator sample.
g) Assigning the Cp values measured in step f) to certain function values of the functions determined in step e).
h) Calculating the quotients of the function values from g) of the target nucleic acid and reference nucleic acid for the sample to be analysed as well as for the calibrator sample.
i) Determining the ratio of the quotients from h) as a measure for the amount of target DNA that was originally present in the sample.

Alternatively such a method according to the invention can be used for the relative quantification of the target nucleic acid relative to a reference nucleic acid and standardized on the basis of a calibrator sample which comprises the following steps:

a) Preparing a common or two separate dilution series of target nucleic acid and reference nucleic acid.
b) Amplifying the various dilutions of target nucleic acid and reference nucleic acid under defined reaction conditions, the amplification of the nucleic acid being measured in real-time.
c) Setting defined signal threshold values for the target nucleic acid and reference nucleic acid.
d) Determining the cycle numbers Cp at which the signal threshold values defined for the target nucleic acid and reference nucleic acid are exceeded in each dilution.
e) Determining a continuously differentiable function of a logarithm of the amounts used of reference nucleic acid as a function of the Cp values determined in d) and determining a continuously differentiable function of a logarithm of the amounts used of reference nucleic acid as a function of the determined Cp.
f) Determination of the Cp values for the target nucleic acid and the reference nucleic acid in the sample to be analysed as well as in a calibrator sample.
g) Assigning the Cp values measured in step f) to certain function values of the functions determined in step e).
h) Calculating the quotients of the function values from g) of the target nucleic acid and reference nucleic acid for the sample to be analysed as well as for the calibrator sample.
i) Determining the ratio of the quotients from h) as a measure for the amount of target DNA that was originally present in the sample.

According to the invention the continuously differentiable functions from step e) which can be linear or non-linear are determined with the aid of a polynomial fit preferably of the $3^{rd}$, $4^{th}$, $5^{th}$, $6^{th}$ or $7^{th}$ degree.

The extent to which the said continuously differentiable functions are linear or non-linear depends on the initial concentrations of the target and reference nucleic acid in the dilution series. With a low initial concentration it can be probably assumed that there will not be a linear relationship between the logarithm of the respective concentration and the Cp values measured for the respective concentration. Apart from this the shape of the said functions depends on the respective experimental conditions and on the respective target sequence and hence these functions have to be determined empirically and cannot be derived on the basis of theoretical considerations.

The described methods for standardization with the aid of a calibrator sample can also be used in particular when the amplification efficiencies change in relation to the initial amounts of target nucleic acid or reference nucleic acid that are to be analysed. As a result the dependence of the amplification efficiencies on the respective original copy numbers of target nucleic acid and reference nucleic acid are indirectly taken into consideration. The quantification methods according to the invention therefore enable even small initial concentrations of target nucleic acid to be determined with high accuracy.

The validity of such a quantification results from the following considerations:

Functions are generated in steps a) to e) of the described method on the basis of the cycle numbers (Cp values) measured for the dilution series which are referred to as calibration curves in the following. The calibration curves are calculated from the individual measured values by means of mathematical methods for example with the aid of a polynomial fit. If the efficiency remains constant for the different initial concentrations of target nucleic acid, the calibration curve is a linear function.

An example of such calibration curves is shown schematically in FIG. 1. The cycle number at which the defined signal threshold value is exceeded is plotted on the abscissa of the graph. The logarithm of a certain relative concentration is plotted on the ordinate of the graph (the base number of the logarithm can be selected at random provided it does not change within the experimental reaction). In this connection the relative concentration is understood as a dimension without a unit which is dependent on the respective detection efficiency but proportional to the amount of target and reference nucleic acid that was actually used.

(In the example of FIG. 1 the amplification efficiency of the reference nucleic acid remains constant for various dilutions. However, in comparison the amplification efficiency of the target nucleic acid is increased at low concentrations).

The cycle numbers (Cp values) for the target nucleic acid (Cp-Tar) and reference nucleic acid (Cp-Ref) at which the defined signal threshold values are exceeded are determined for the sample to be analysed in the following steps f) and g) of the described method. Function values log (Rconc (Tar)) and log (Rconc (Ref)) are assigned to the cycle numbers Cp-Tar and Cp-Ref determined for the sample on the basis of the previously determined calibration curves.

In the case of a relative quantification it is additionally advantageous to eliminate the influence of different detection efficiencies for the target nucleic acid and reference nucleic acid. This can be achieved with the aid of a so-called calibrator sample. Hence the Cp values for the target nucleic acid and reference nucleic acid are also determined for a calibrator sample in the same manner as for the sample to be analysed and also assigned corresponding function values.

However, in the following it is assumed that the detection efficiency remains constant during an experiment i.e. an experimentally determined relative concentration is proportional to the copy number of target and reference nucleic acid that are actually present in the respective sample. Thus the following firstly applies for any sample including the calibrator:

$$AConc(Tar) = K_{Tar} \times Rconc(Tar) \qquad (1)$$

$$AConc(Ref) = K_{Ref} \times Rconc(Ref) \qquad (2)$$

in which

AConc(Tar)=the actual copy number of target nucleic acid present in a sample

AConc(Ref)=the actual copy number of reference nucleic acid present in a sample $K_{Tar}$=const $K_{Ref}$=const Rconc (Tar)=relative concentration of the target nucleic acid (without a unit)

Rconc (Ref)=relative concentration of the reference nucleic acid (without a unit)

The constants $K_{Tar}$ and $K_{Ref}$ are quantities whose absolute values depend on the respective detection efficiency. In other words these constants take into consideration factors such as a different quantum yield of the fluorescent labels or different hybridization kinetics of the hybridization probes and are therefore usually not identical.

The following quotient is formed according to step h) of the method described above $$\frac{Rconc(Tar)}{Rconc(Ref)}$$

from (1) and (2) it follows:

$$\frac{Rconc(Tar)}{Rconc(Ref)} = \frac{K_{(Ref)} \times Aconc(Tar)}{K_{(TAR)} \times Aconc(Ref)} \qquad (3)$$

This equation applies equally to the sample to be analysed as well as to the calibration sample since the same detection agent is used for both samples.

$$\frac{Rconc(Tar)_{cal}}{Rconc(Ref)_{cal}} = \frac{K(Ref)}{K(Tar)} \times \frac{Aconc(Tar)_{cal}}{Aconc(Ref)_{cal}} \qquad (4)$$

According to step i) of the method described above the ratio of the two determined quotients is subsequently determined:

$$\frac{\frac{Rconc(Tar)}{Rconc(Ref)}}{\frac{Rconc(Tar)_{cal}}{Rconc(Ref)_{cal}}} = \frac{\frac{K(Ref) \times Aconc(Tar)}{K(Tar) \times Aconc(Ref)}}{\frac{K(Ref) \times Aconc(Tar)_{cal}}{K(Tar) \times Aconc(Ref)_{cal}}} \qquad (5)$$

Consequently the constants that are dependent on the respective detection efficiency can be eliminated:

$$\frac{\frac{Rconc(Tar)}{Rconc(Ref)}}{\frac{Rconc(Tar)_{cal}}{Rconc(Ref)_{cal}}} = \frac{\frac{Aconc(Tar)}{Aconc(Ref)}}{\frac{Aconc(Tar)_{cal}}{Aconc(Ref)_{cal}}} \qquad (6)$$

It follows that the ratios of the determined relative concentrations of target nucleic acid to reference nucleic acid standardized on the basis of the ratio of the relative concentrations of target nucleic acid to reference nucleic acid in the calibrator are identical to the ratios of the absolute copy numbers of target nucleic acid and reference nucleic acid in the individual samples to be analysed.

Hence this method according to the invention is an exact method for the relative quantification of nucleic acids in which on the one hand, different efficiencies of PCR reactions are taken into account without having to directly determine the efficiency and on the other hand, the influence of the detection efficiency which depends on various uncontrollable factors is eliminated due to the use of a calibrator sample.

The invention is further elucidated by the following examples:

EXAMPLE 1

Amplification of Cyclophylin A (CycA) and Porphobilinogen Deaminase (PBGD) cDNAs cDNAs were synthesized with the aid of a reverse transcriptase reaction from 3 commercially available (Clontech) total RNAs isolated from a HeLa cell line, adrenal gland tissue and brain tissue under the following conditions:

1 µg total RNA
1×AMV reaction buffer
5 mM $MgCl_2$
1 mM deoxynucleotide mix 0.0625 mM randomized hexamers
50 units RNase
10 units AMV reverse transcriptase
ad 20 μl H$_2$O All mixtures were incubated for 10 minutes at 25° C., 60 minutes at 42° C. and 5 minutes at 95° C. for the cDNA synthesis. Then they were cooled to 4° C.

Afterwards the amplification reaction was carried out which was measured in real-time in the FRET HybProbe format on a LightCycler instrument (Roche Diagnostics GmbH). Each mixture was amplified under the following conditions:
1×LC-fast start DNA-master hybridization probes (Roche Diagnostics GmbH)
3 m M MgCl$_2$
0.5 mM of each primer
0.2 μM fluorescein probe
0.2 μM LC-RED640 probe
ad 20 μl H$_2$O Primers having SEQ. ID. NO:1 and SEQ. ID. NO: 2 were used to amplify the CycA sequence (Cyclophilin A). The CycA product was detected using a fluorescein-labelled probe having SEQ. ID. NO: 3 and a LC-RED640-labelled probe having SEQ. ID. NO: 4. Primers having SEQ. ID. NO:5 and SEQ. ID. NO: 6 were used to amplify the PBGD sequence (porphobilinogen). The PBGD product was detected using a fluorescein-labelled probe having SEQ. ID. NO: 7 and a LC-RED640-labelled probe having SEQ. ID. NO: 8.

The preparation was amplified under the following PCR conditions in the LightCycler:

| denaturation: 95° C. | 10 min | | |
| amplification: 45× | 95° C. | 10 sec | 20.0° C./sec |
| | 55° C. | 10 sec | 20.0° C./sec |
| | 72° C. | 15 sec | 3.0° C./sec |
| cooling: | 40° C. | 30 sec | |

After each incubation at 55° C. a fluorescence measurement was carried out according to the manufacturer's instructions. The signal threshold value (Cp value) was determined as the maximum of the 2$^{nd}$ derivative of the amplification reaction as a function of the cycle number.

EXAMPLE 2

Determination of the Efficiency of the Amplification of CycA and PBGD

The cDNA synthesized from HeLa total RNA was diluted in 1:5 steps (a total of 5 dilution steps) in order to determine the amplification efficiencies of CycA and PBGD. A 3-fold determination of the signal threshold value (Cp value) was carried out on the LightCycler for each dilution step. This was carried out for CycA as well as for PBGD.

Two different functions were generated in order to determine the fit coefficients in which the cycle number Cp was determined for each concentration as a function of the decadic logarithm of the cDNA concentration used.

a) Generation of a linear function:

Assuming identical efficiencies for the various initial concentrations of a nucleic acid, the two respective amplification efficiencies for the target nucleic acid and reference nucleic acid were determined according to the equation $$E = G \frac{-1}{f(\log(conc))}.$$

Figure 2A:
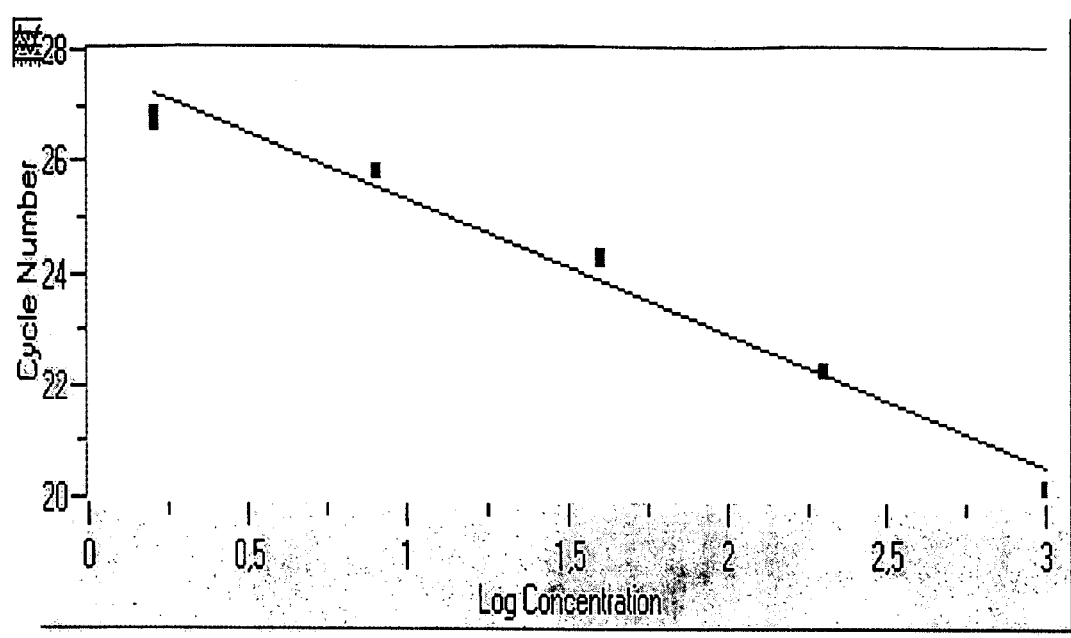
FIG. 2a:
Determination of the amplification efficiency of CycA by determining a regression line.
Figure 2B:
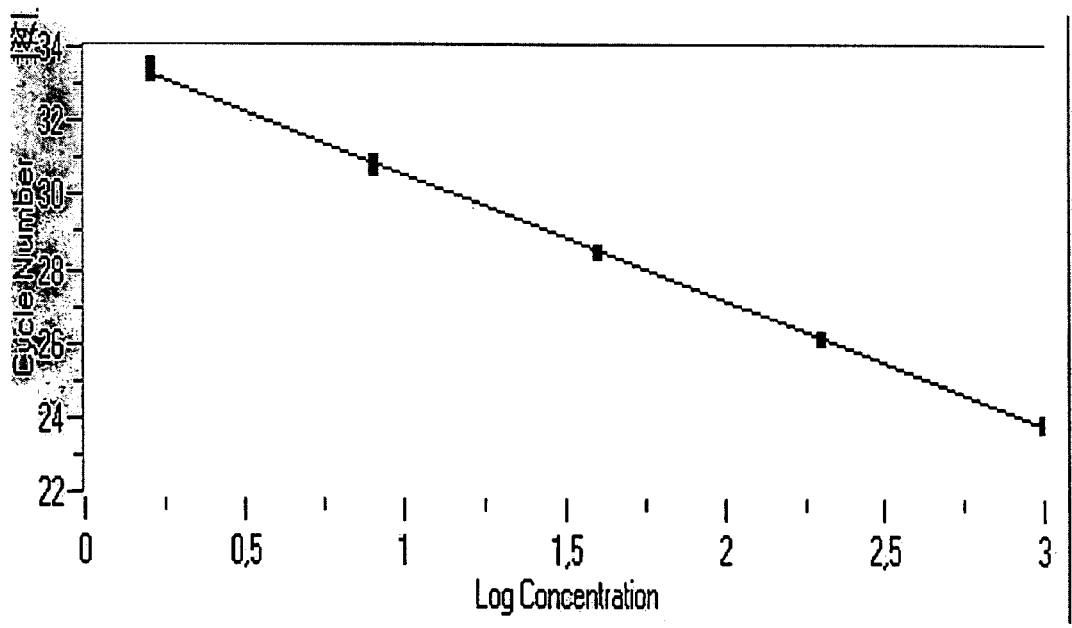
FIG. 2b:
Determination of the amplification efficiency of PBGD by determining a regression line.
Figure 3A:
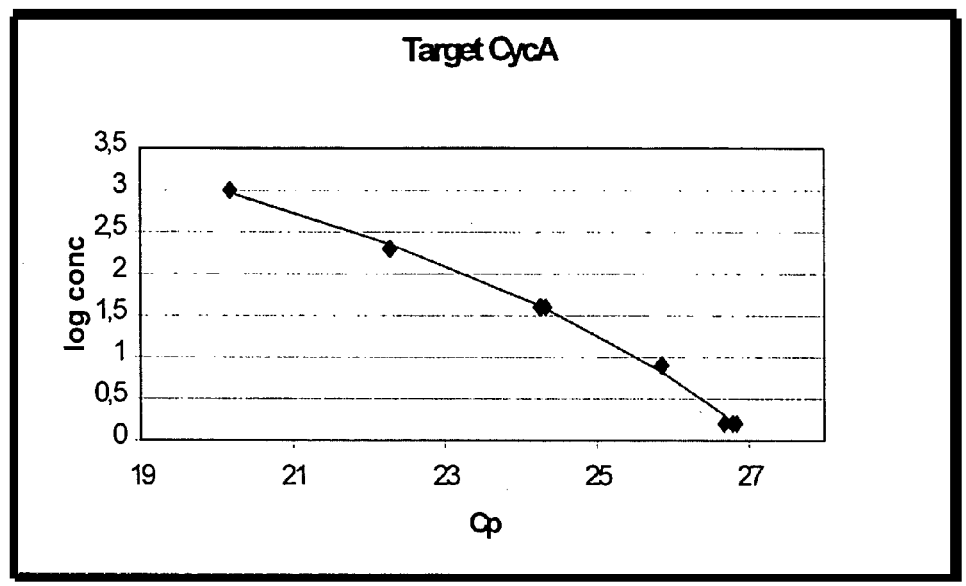
FIG. 3a:
Efficiency correction for the amplification of CycA with the aid of a polynomial fit of the $4^{th}$ degree.
Figure 3B:
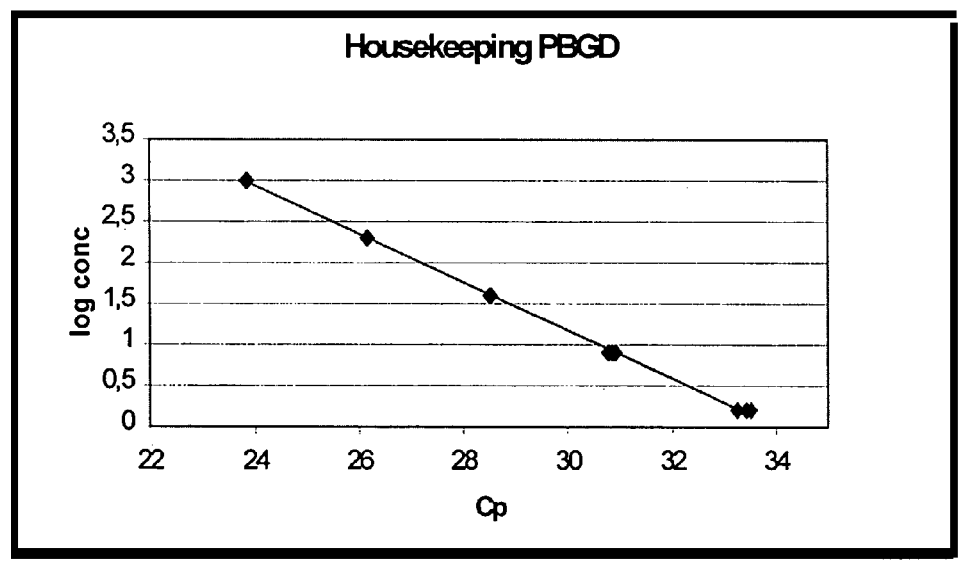
FIG. 3b:
Efficiency correction for the amplification of PBGD with the aid of a polynomial fit of the $4^{th}$ degree.

In this case f (log(conc)) was determined as the slope of the regression line of the functions shown in FIGS. 2a and 2b. Thus an efficiency E=2.62 was determined for the target nucleic acid CycA and an efficiency E=1.97 was determined for the reference nucleic acid PBGD.

b) Generation of a non-linear function with the aid of a polynomial fit of the 4$^{th}$ degree according to the invention The same measured values were used to generate target and reference nucleic acid functions of the logarithm of the determined relative concentrations versus the measured Cp values by calculating a polynomial fit of the 4$^{th}$ degree. These functions are shown in FIGS. 3a (target nucleic acid) and 3b (reference nucleic acid).

The determined fit parameters for the target nucleic acid (CycA) were:
A(Offset)=11.3974946
B(linear)=−0.1
C(quadrat.)=−0.0721349
D=0.0044516
E=−8.214E-05

The determined fit parameters for the reference nucleic acid were:
A(Offset)=9.98347024
B(linear)=−0.29359011
C=0
D=0
E=0

As can be seen from the figures and the determined fit parameters, this results in an almost linear function for the reference nucleic acid. Consequently amplification of the reference nucleic acid in the measured concentration range occurs with largely constant efficiency.

In contrast a non-linear function was determined with the Cp values obtained for the target nucleic acid CycA. Hence the efficiency of the amplification reaction in the measured concentration range for CycA is significantly dependent on the original copy number present in the sample.

EXAMPLE 3

Calibrator-standardized Determination of the Original Ratio of Target and Reference Nucleic Acid With and Without an Implied Correction of the Amplification Efficiency Under the conditions described in Example 1 the ratio determined of the original amount of CycA and PBGD should be independent of the respective amplified amount of the sample material used. Hence the determination of the ratio of various amounts of sample RNA were used to check the effect of an efficiency correction on the basis of the measured values that were obtained.

The original ratios of target (CycA) and reference (PBGD) nucleic acid in adrenal gland RNA and brain RNA were determined using three dilution steps in each case of the cDNAs (duplicate determinations were carried out for each dilution step). The quotient of the ratio of the relative concentrations CycA and PBGD were determined from the measured data between the analysed sample and the calibrator sample. Total RNA from HeLa cells was used as the calibrator. This determination was carried out, on the one hand, with an assumed amplification efficiency of 2.00 for CycA and PBGD, on the other hand, with the aid of the linear and non-linear functions determined in Example 2.

Table 1 shows the calibrator-standardized ratios of target/reference nucleic acid

|  | without efficiency correction | efficiency correction with a linear fit function | implicit efficiency correction with a non-linear fit function |
|---|---|---|---|
| adrenal gland 40 ng | 1.03 | 1.18 | 1.41 |
| adrenal gland 8 ng | 2.21 | 1.79 | 1.19 |
| adrenal gland 1.6 ng | 6.00 | 4.17 | 1.93 |
| mean | 3.08 | 2.38 | 1.51 |
| standard deviation | 2.5967 | 1.5799 | 0.3800 |
| coefficient of variation | 84.3% | 66.4% | 25.2% |
| maximum error in %* (maximum value/minimum value − 1) × 100 | 483% | 253% | 62% |
| brain 40 ng | 1.61 | 2.14 | 2.92 |
| brain 8 ng | 2.48 | 2.11 | 1.60 |
| brain 1.6 ng | 6.68 | 4.66 | 2.54 |
| maximum error in % | 315% | 121% | 82% |
| mean | 3.59 | 2.97 | 2.35 |
| standard deviation | 2.7111 | 1.4637 | 0.6795 |
| coefficient of variation | 75.5% | 49.3% | 28.9% |
| maximum error in %* (maximum value/minimum value − 1) × 100 | 75.5% | 49.3% | 28.9% |

As shown in Table 1 the values determined for the two sample RNAs (adrenal gland and brain tissues) after an inventive non-linear efficiency correction have a ca. three-fold lower coefficient of variation compared to the same values without an efficiency correction and a ca. two-fold lower coefficient of variation than the same values with a linear efficiency correction. Also the percentage maximum error of the calibrator-standardized target/reference ratios as a function of the initial concentration is also significantly reduced by the inventive non-linear efficiency correction for the two target RNAs compared to the linear efficiency correction or compared to the method without an efficiency correction. These results show that the inventive method is particularly advantageous in methods in which a standardization is carried out with the aid of calibrators.

The present invention is not to be limited in scope by the exemplified embodiments which are intended as illustrations of single aspects of the invention. Various modifications of the invention in addition to those described herein will become apparent to those skilled in the art from the foregoing description and accompanying drawings. Such modifications are intended to fall within the scope of the appended claims. All publications cited herein are incorporated by reference in their entirety.

What is claimed is:

1. A method for quantification of a target nucleic acid relative to a reference nucleic acid and standardized with a calibrator sample comprising the steps of:

(a) preparing a common or two separate dilution series of target nucleic acid and reference nucleic acid;

(b) amplifying the various dilutions of target nucleic acid and reference nucleic acid under defined reaction conditions, and measuring the amplification of the nucleic acids in real-time;

(c) setting defined signal threshold values for the target nucleic acid and reference nucleic acid;

(d) determining the cycle numbers Cp at which the signal threshold values defined for the target nucleic acid and reference nucleic acid are exceeded in each dilution;

(e) determining a continuously differentiable function of the Cp values determined in step d) as a function of the logarithm of the amounts used of target nucleic acid and determining a continuously differentiable function of the Cp values determined in step d) as a function of the logarithm of the amounts used of reference nucleic acid;

(f) determining the Cp values of the target nucleic acid and reference nucleic acid in a sample to be analysed as well as in a calibrator sample;

(g) assigning the Cp values measured in step f) to particular values of the functions determined in step e);

(h) calculating (1) the quotient of the function values from step g) of the target nucleic acid and reference nucleic acid for the sample to be analysed, and (2) the quotient of the function value from step g) of the target nucleic acid and the reference nucleic acid in the calibrator sample; and (i) determining the ratio of the two quotients from step h) as a measure of the original amount of target nucleic acid contained in the sample to be analysed.

2. A method for quantification of a target nucleic acid relative to a reference nucleic acid and standardized with a calibrator sample comprising the steps of:

(a) preparing a common or two separate dilution series of target nucleic acid and reference nucleic acid;
(b) amplifying the various dilutions of target nucleic acid and reference nucleic acid under defined reaction conditions, and measuring the amplification of the nucleic acids in real-time;
(c) setting defined signal threshold values for the target nucleic acid and reference nucleic acid;
(d) determining the cycle numbers Cp at which the signal threshold values defined for the target nucleic acid and reference nucleic acid are exceeded in each dilution;
(e) determining a continuously differentiable function of the logarithm of the amounts used of target nucleic acid as a function of the Cp values determined in step d) and determining a continuously differentiable function of the logarithm of the amounts used of reference nucleic acid as a function of the Cp values determined in step d);
(f) determining the Cp values of the target nucleic acid and reference nucleic acid in a sample to be analysed as well as in a calibrator sample;
(g) assigning the Cp values measured in step f) to particular values of the functions determined in step e);
(h) calculating (1) the quotient of the function values from step g) of the target nucleic acid and reference nucleic acid for the sample to be analysed, and (2) the quotient of the function value from step g) of the target nucleic acid and the reference nucleic acid in the calibrator sample; and
(i) determining the ratio of the two quotients from step h) as a measure of the original amount of target nucleic acid contained in the sample to be analysed.

3. The method of claim 2, wherein the continuously differentiable functions from step e) are determined with a polynomial fit.

4. The method of claim 2, wherein the amplified nucleic acids are detected with at least one fluorescently-labeled hybridization probe.

5. The method of claim 4, wherein the amplified nucleic acids are detected with fluorescence resonance energy transfer (FRET) hybridization probes, molecular beacons, or TAQMAN® probes.

6. The method of claim 2, wherein the amplified nucleic acids are detected with a DNA-binding dye.

* * * * *